US012588933B2

(12) United States Patent
Biedermann et al.

(10) Patent No.: US 12,588,933 B2
(45) Date of Patent: Mar. 31, 2026

(54) COUPLING DEVICE FOR COUPLING A ROD TO A BONE ANCHOR

(71) Applicant: BIEDERMANN TECHNOLOGIES GMBH & CO. KG, Donaueschingen (DE)

(72) Inventors: Timo Biedermann, Trossingen (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 18/301,136

(22) Filed: Apr. 14, 2023

(65) Prior Publication Data

US 2023/0320756 A1 Oct. 12, 2023

Related U.S. Application Data

(63) Continuation of application No. 17/511,397, filed on Oct. 26, 2021, now Pat. No. 11,660,123.

(Continued)

(30) Foreign Application Priority Data

Oct. 29, 2020 (EP) ..................................... 20204581

(51) Int. Cl.
| | |
|---|---|
| *A61B 17/86* | (2006.01) |
| *A61B 17/70* | (2006.01) |
| *A61B 17/00* | (2006.01) |

(52) U.S. Cl.
CPC ...... *A61B 17/7008* (2013.01); *A61B 17/7032* (2013.01); *A61B 17/8605* (2013.01); *A61B 17/8625* (2013.01); *A61B 2017/00477* (2013.01)

(58) Field of Classification Search
None
See application file for complete search history.

(56) References Cited

U.S. PATENT DOCUMENTS

| | | | |
|---|---|---|---|
| 10,555,759 B2 | 2/2020 | Krüger | |
| 2009/0105769 A1* | 4/2009 | Rock .................. | A61B 17/7038 606/301 |

(Continued)

FOREIGN PATENT DOCUMENTS

| | | |
|---|---|---|
| EP | 2 174 608 A1 | 4/2010 |
| EP | 2 826 429 A1 | 1/2015 |

(Continued)

OTHER PUBLICATIONS

Extended European Search Report for Application No. 20204581.1, mailed May 3, 2021, 7 pages.

*Primary Examiner* — Tessa M Matthews
(74) *Attorney, Agent, or Firm* — Womble Bond Dickinson (US) LLP

(57) ABSTRACT

A coupling device for coupling a rod to a bone anchor includes a receiving part configured to receive a head of the bone anchor, the receiving part having a first end and a second end, a central axis that extends between the first and second ends, and two legs at the first end that define a recess extending in a longitudinal direction transverse to the central axis for receiving the rod, and a monolithic pressure member positionable in the receiving part, the pressure member including a rod support surface and an engagement portion to adjust the pressure member to exert pressure on the head. The engagement portion is positioned farther radially from the central axis in the longitudinal direction than a first portion of the rod support surface, and extends closer axially to the first end of the receiving part than the entire first portion of the rod support surface.

20 Claims, 13 Drawing Sheets

Related U.S. Application Data

(60) Provisional application No. 63/107,033, filed on Oct. 29, 2020.

(56)                    References Cited

U.S. PATENT DOCUMENTS

| | | | |
|---|---|---|---|
| 2011/0251664 A1* | 10/2011 | Acosta De Acevedo | .................... A61F 2/954 623/1.11 |
| 2012/0143266 A1 | 6/2012 | Jackson et al. | |
| 2014/0121703 A1* | 5/2014 | Jackson | ............. A61B 17/7032 606/246 |
| 2018/0153600 A1 | 6/2018 | Koller et al. | |
| 2019/0209214 A1 | 7/2019 | Biedermann et al. | |

FOREIGN PATENT DOCUMENTS

| | | | | |
|---|---|---|---|---|
| EP | 3 158 957 A1 | 4/2017 | | |
| WO | WO 2012/064360 A1 | 5/2012 | | |
| WO | WO-2020097691 A1 * | 5/2020 | ......... | A61B 17/7032 |

* cited by examiner

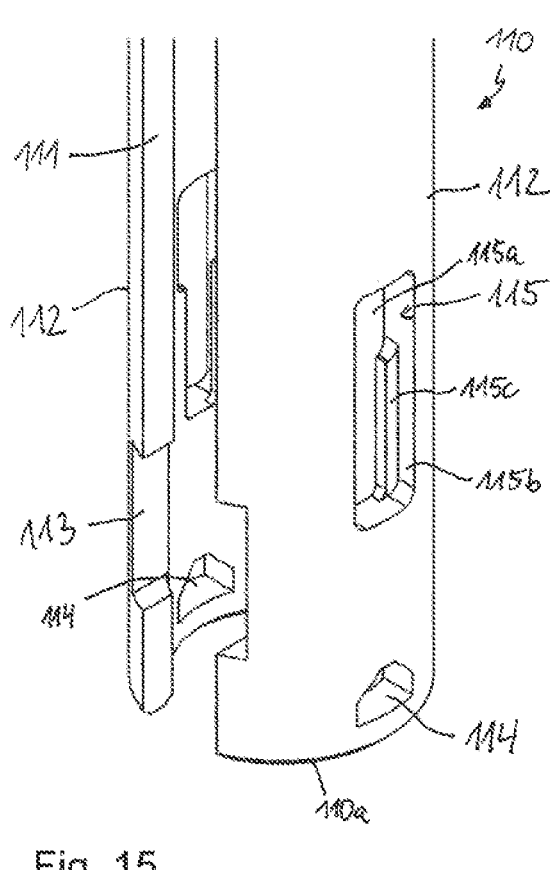
Fig. 15
Fig. 16
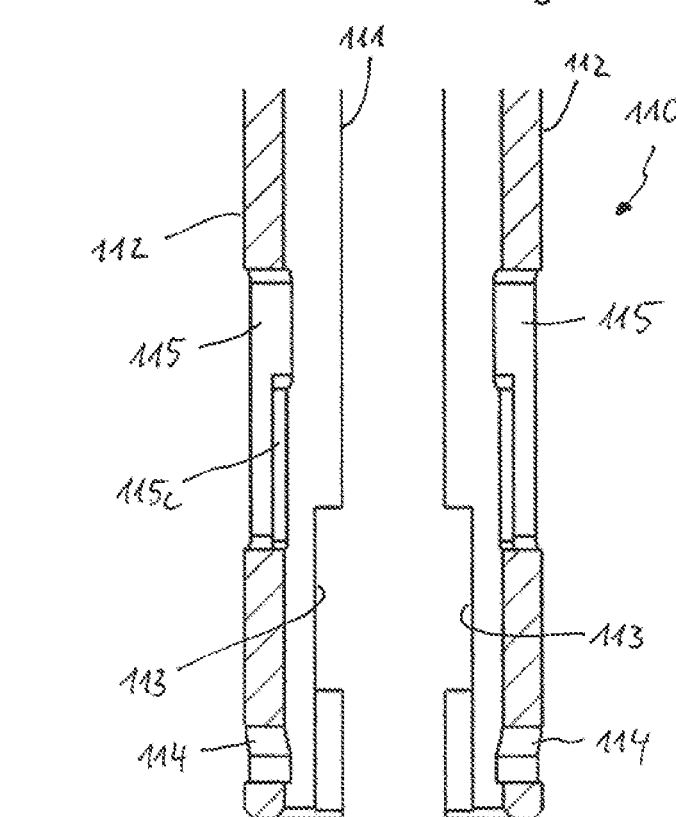
Fig. 17

COUPLING DEVICE FOR COUPLING A ROD TO A BONE ANCHOR

CROSS-REFERENCE TO RELATED APPLICATION(S)

This application is a continuation of U.S. patent application Ser. No. 17/511,397, filed Oct. 26, 2021, which application claims priority to and the benefit of U.S. Provisional Patent Application No. 63/107,033, filed Oct. 29, 2020, the contents of which are hereby incorporated by reference in their entirety, and claims priority from European Patent Application EP 20 204 581.1, filed Oct. 29, 2020, the contents of which are hereby incorporated by reference in their entirety.

BACKGROUND

Field

The application relates to a coupling device for coupling a rod to a bone anchor. In particular, the application relates to a polyaxial bone anchoring device that permits temporarily or permanently locking of a polyaxial position of the bone anchor independently of the rod. Such a coupling device may be applicable in the treatment of deformities or other diseases or injuries of the spine.

Description of Related Art

A polyaxial pedicle screw having provisional fastening means is, for example, known from U.S. Pat. No. 10,555,759 B2. The polyaxial pedicle screw includes a screwed shaft section for anchoring the pedicle screw in a vertebra, on one axial end of which a shaft head is configured which is coupled in a rotating and/or pivoting manner to a receiving sleeve for a longitudinal support. The receiving sleeve has a fastening means for selective positional fastening of the receiving sleeve with respect to the shaft section. The fastening means consists at least of an inlay mounted in the receiving sleeve and acting on the shaft head, and a locking element acting on the inlay. The inlay is configured with attachment points or engagement elements, which are not covered or overlapped by the locking element, for the provisional introduction of a compressive force on the inlay parallel to the locking element. The basic idea thereof is based on causing the provisional/temporary fixing (locking) of the polyaxiality by means of an external helping means, which acts on the inlay and the receiving sleeve in order to bias these against each other and thereby clamp the shaft head.

In US 2019/0209214 A1, a polyaxial bone anchoring device is described that includes a receiving part with two legs defining a recess for receiving a rod, and a pressure member for exerting pressure on a head of a bone anchor in the receiving part. The pressure member has an engagement portion that extends at least partially into a leg of the receiving part and is directly engageable from outside the bone anchoring device. With an instrument, for example, the pressure member can be adjusted from a non-locking position where the head is pivotable to a locking position where the head is clamped.

SUMMARY

In spinal surgery, often multiple segments of the spinal column are corrected and/or stabilized using a spinal rod and polyaxial bone anchors. During such a procedure, repeated adjustments of the bone anchor and the rod relative to a receiving part of a polyaxial bone anchoring device may become necessary. Therefore, there is a need for simple and effective handling of the polyaxial bone anchoring device in terms of locking and unlocking of the head and the rod during correction steps.

It is an object of the invention to provide an improved coupling device and an improved polyaxial bone anchoring device, as well as a system including such a coupling device or such a polyaxial bone anchoring device, and an instrument that is convenient to operate and/or effective in terms of locking.

According to an embodiment, the coupling device includes a receiving part configured to receive a head of the bone anchor, the receiving part having a first end and a second end, a central axis extending through the first end and the second end, and a recess at the first end for receiving the rod, the recess forming two legs and defining a longitudinal direction corresponding to the extension of an inserted rod. A pressure member is configured to be arranged at least partially in the receiving part to exert pressure on an inserted head, the pressure member having a rod support surface for supporting an inserted rod and an engagement portion engageable to cause the pressure member to exert pressure on an inserted head. The engagement portion is located at a position outside of the legs in the longitudinal direction and projects above the rod support surface.

The coupling device permits clamping or locking of the head of the bone anchor independently of whether there is a rod inserted into the coupling device. Moreover, the coupling device permit such clamping or locking of the head independently of whether a fixation member for fixing the rod is already inserted.

The clamping of the head of the bone anchor may be temporary or permanent. Temporary fixation may be achieved with an instrument which acts only on the pressure member without acting on the rod. In this case the head may be locked at an angular position with respect to the receiving part as long as the instrument acts on the pressure member.

A permanent fixation may be achieved, for example, using a fixation member that acts only on the pressure member without acting on the rod. In this case, the rod may be kept sliding in the coupling device. Such a sliding rod construct may be useful, for example, in the treatment of scoliosis in children.

Thus, a coupling device according to embodiments of the invention increases possibilities during surgery. In addition, the steps of adjusting an angular position of the coupling device relative to the bone anchor can be carried out repeatedly in a quick and easy manner.

According to an embodiment, an instrument for use with the coupling device includes a first instrument portion, preferably an outer tube, the first instrument portion being configured to engage the receiving part, and a second instrument portion, preferably arranged at least partially in the first instrument portion, and being displaceable relative to the first instrument portion, the second instrument portion being configured to engage the engagement portion of the pressure member. When the first instrument portion engages the receiving part and the second instrument portion engages the engagement portion, the pressure member is movable from a non-locking position in which an inserted head is pivotable in the receiving part to a locking position in which the head is clamped.

The instrument may be designed such that the recess of the receiving part that receives the rod can remain unobstructed during the locking of the head of the bone anchor. In this way it may be possible to temporarily clamp or lock the head of the bone anchor while a rod and/or a fixation member is not yet placed in the rod channel, or while the rod is at a higher position above the bottom of the rod channel. This also may increase possibilities for surgical correction steps.

The engagement between the instrument and the engagement portion of the pressure member may be a pressing contact, free from a form-fit engagement. This may render the engagement step simple and fast.

The bone anchoring device may be a bottom-loading bone anchoring device where the head of the bone anchor is insertable from a lower end of the receiving part, or may be a top-loading bone anchoring device where the bone anchor is insertable into the receiving part from an upper end of the receiving part.

BRIEF DESCRIPTION OF THE DRAWINGS

Further features and advantages of the invention will become apparent from the description of embodiments by means of the accompanying drawings. In the drawings:

FIG. 15 shows a perspective view from a top of a front portion of an outer member of the instrument of FIG. 14.

FIG. 16 shows a perspective view from a bottom of the front portion of FIG. 15.

FIG. 17 shows a cross-sectional view of the front portion of the outer member shown in FIGS. 15 and 16, the cross-section taken in a plane including a central longitudinal axis of the instrument and extending through centers of two arms of the outer member.

FIGS. 21*a* to 21*d* show perspective views of steps of attaching the instrument of FIGS. 14 to 20 to the polyaxial bone anchoring device of FIGS. 1 and 2, wherein FIG. 21*c* shows an enlarged portion of FIG. 21*b*.

DETAILED DESCRIPTION

Figures 1, 2:
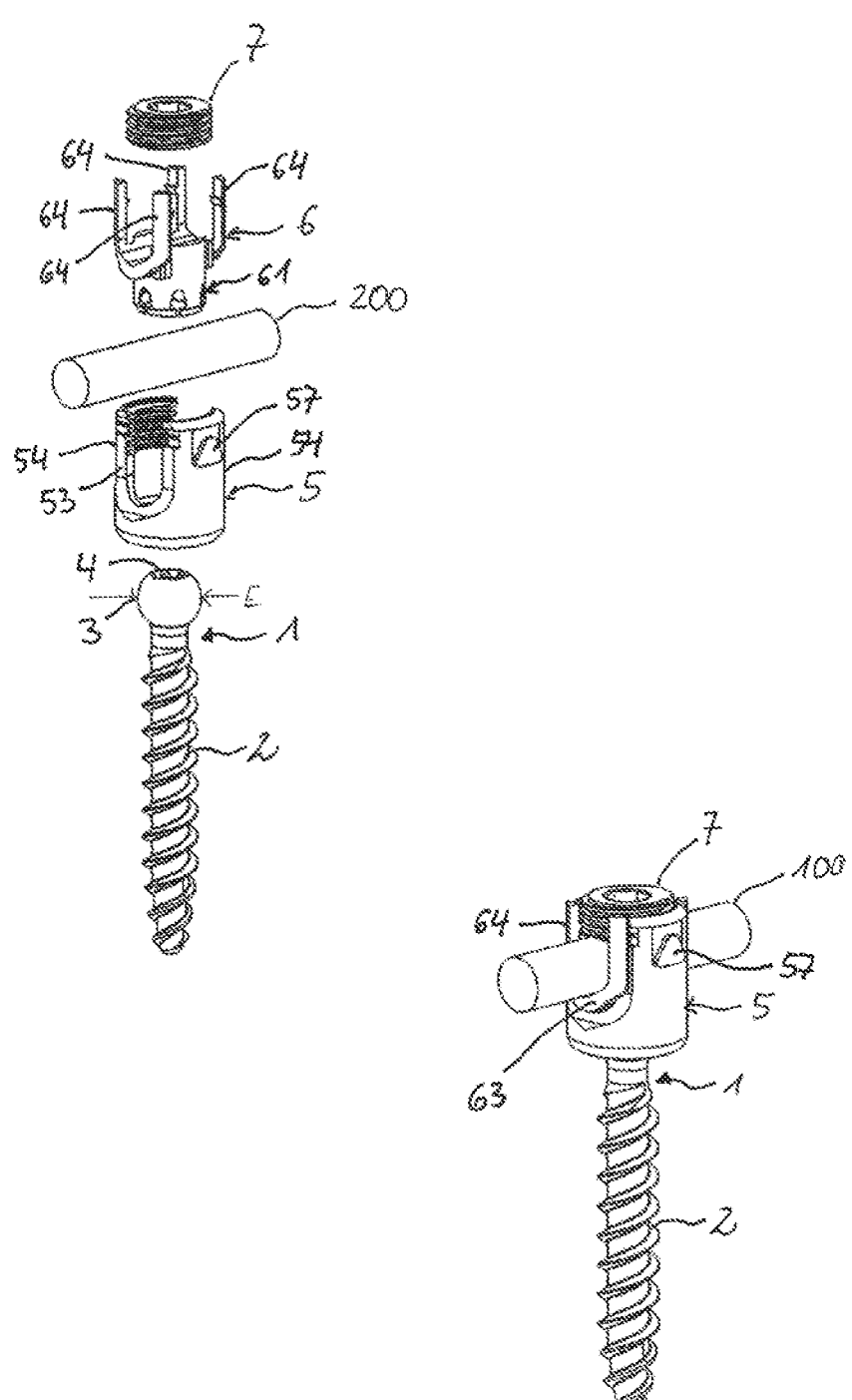
FIG. 1 shows a perspective exploded view of a first embodiment of a polyaxial bone anchoring device that includes a coupling device.
FIG. 2 shows a perspective view of the polyaxial bone anchoring device of FIG. 1 in an assembled state.
Figure 11:
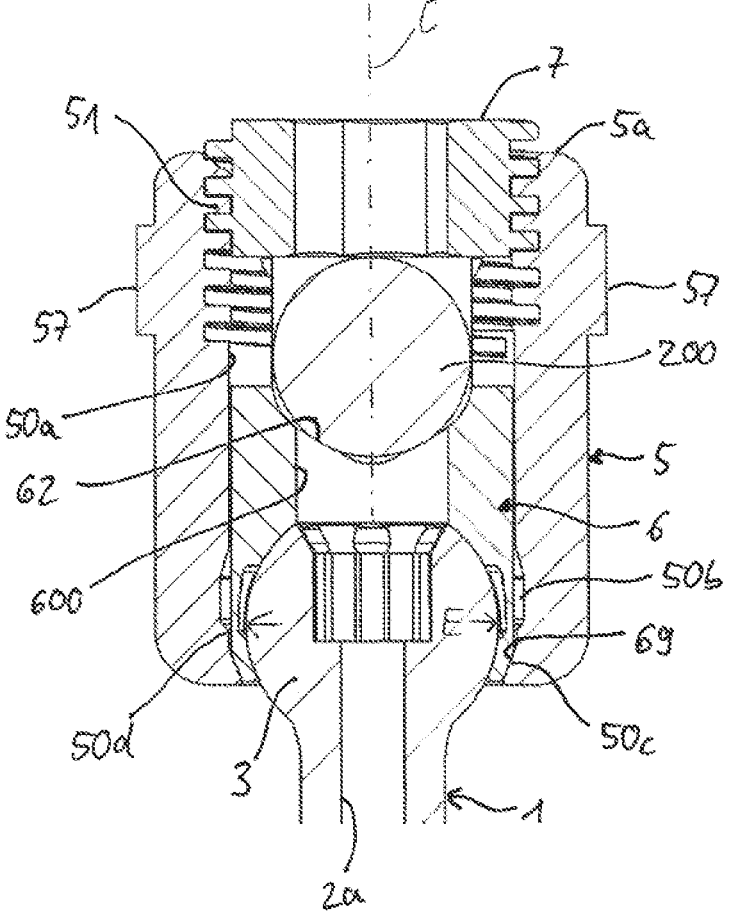
FIG. 11 shows a cross-sectional view of the polyaxial bone anchoring device of FIGS. 1 and 2, the cross-section taken in a plane extending through the central axis of the receiving part and through centers of the legs of the receiving part.

As depicted in FIGS. 1 and 2, a bone anchoring device according to an embodiment of the invention includes a bone anchor 1 in the form of, for example, a bone screw having a shank 2 with a threaded portion and a head 3 with a spherically-shaped outer surface portion. The head 3 may have a recess 4 for engagement with a drive tool. As shown in FIG. 11, for example, the bone anchor may also have a channel 2*a* extending therethrough. The bone anchoring device also includes a coupling device that includes a receiving part 5 for receiving a rod 200 to be connected to the bone anchor 1. In addition, a pressure member 6 forms a part of the coupling device. The pressure member is arranged in the receiving part and is configured to exert pressure on the head 3 of the bone anchor 1 to clamp and/or finally lock the head 3 with respect to the receiving part 5. Furthermore, a fixation member 7 may be part of the bone anchoring device for fixing the rod in the receiving part 5. The fixation member 7 may be, for example, an inner screw or set screw, that is configured to exert a force on the rod.

The receiving part 5 will be described in greater detail, referring additionally to FIGS. 3 to 6. The receiving part 5 includes a first end 5*a* forming an upper end and an opposite second end 5*b* forming a lower end, and a central axis C that passes through the first end 5*a* and the second end 5*b*. The overall outer shape of the receiving part may be substantially cylindrical, except for structures such as projections and grooves or recesses that are formed on or in the cylindrical surface. A passage 50 extends through the receiving part 5 from the first end 5a to the second end 5b. The passage 50 may have several sections having different diameters. In the embodiment, the passage has a first coaxial bore 50a starting at or close to the first end 5a and extending to a distance from the first end 5a. At least a portion of the first coaxial bore 50a is provided with an internal thread 51 that preferably starts at the first end. Between the first coaxial bore 50a and the second end 50b, a widened section in the form of a second coaxial bore 50b may be provided that permits a portion of the pressure member 6 to expand therein. Between the second end 5b and the second coaxial bore 50b, a narrowing portion 50c is formed that narrows, for example, in a conical shape, towards the second end 5b. It shall be noted that transition portions may be formed between the first coaxial bore 50a and the second coaxial bore 50b on the one hand, and between the narrowing portion 50c and the second coaxial bore 50b on the other hand. For example, an edge 50d may be provided between the narrowing portion 50c and the second coaxial bore 50b that may contribute to compressing a portion of the pressure member 6, as explained below. By the passage 50, an opening 52 is formed at the second end 5b, a width of which is greater than a greatest outer diameter E of the head 3. Hence, the receiving part 5 is suitable for inserting the head 3 of the bone anchor 1 through the opening 52 at the second end 5b into the receiving part 5.

Figures 3, 4, 5, 6:
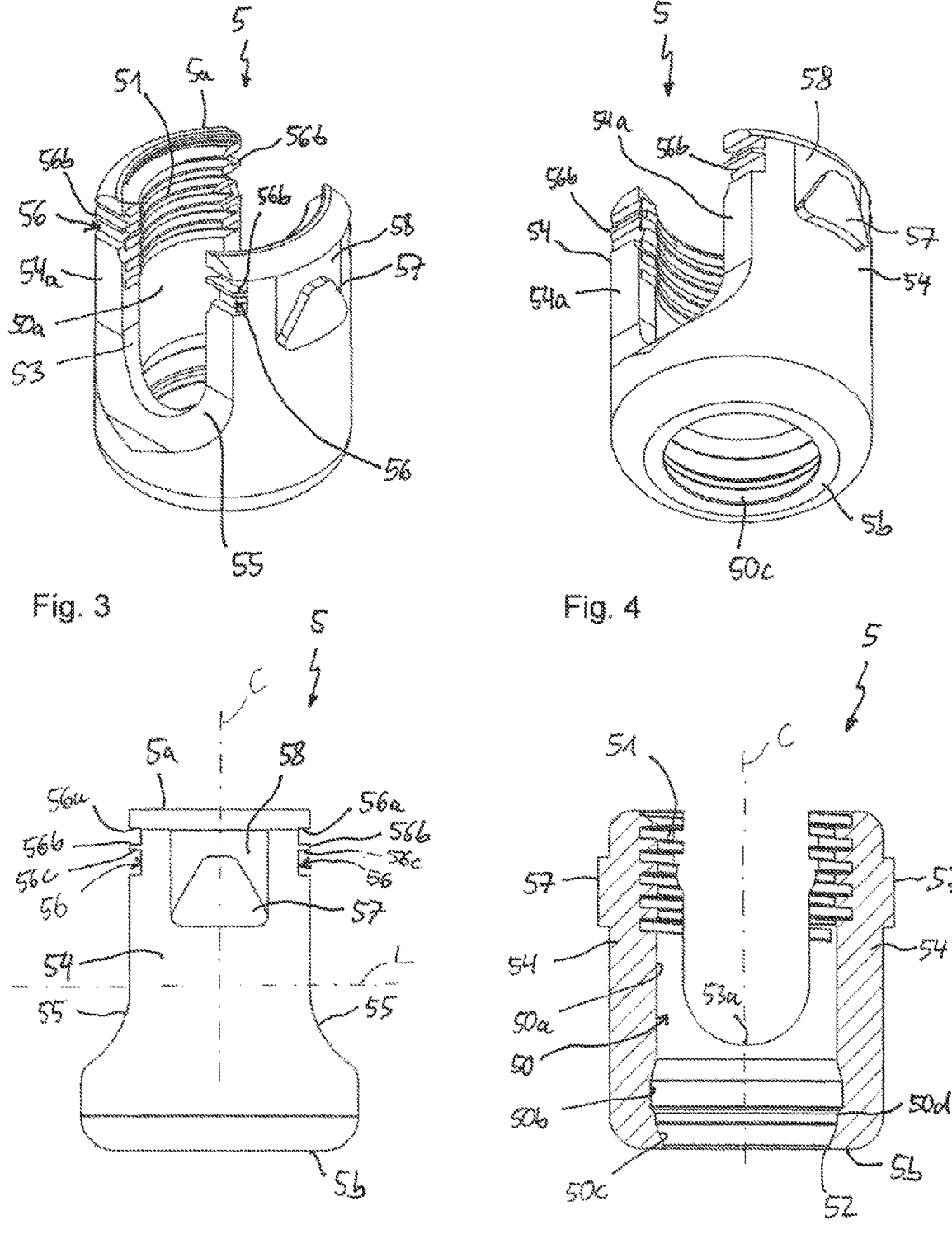
FIG. 3 shows a perspective view from a top of a receiving part of the polyaxial bone anchoring device of FIGS. 1 and 2.
FIG. 4 shows a perspective view from a bottom of the receiving part of FIG. 3.
FIG. 5 shows a side view of the receiving part of FIGS. 3 and 4.
FIG. 6 shows a cross-sectional view of the receiving part of FIGS. 3 to 5, the cross-section taken in a plane including a central axis of the receiving part and extending through centers of legs of the receiving part.
Figures 7, 8, 9, 10:
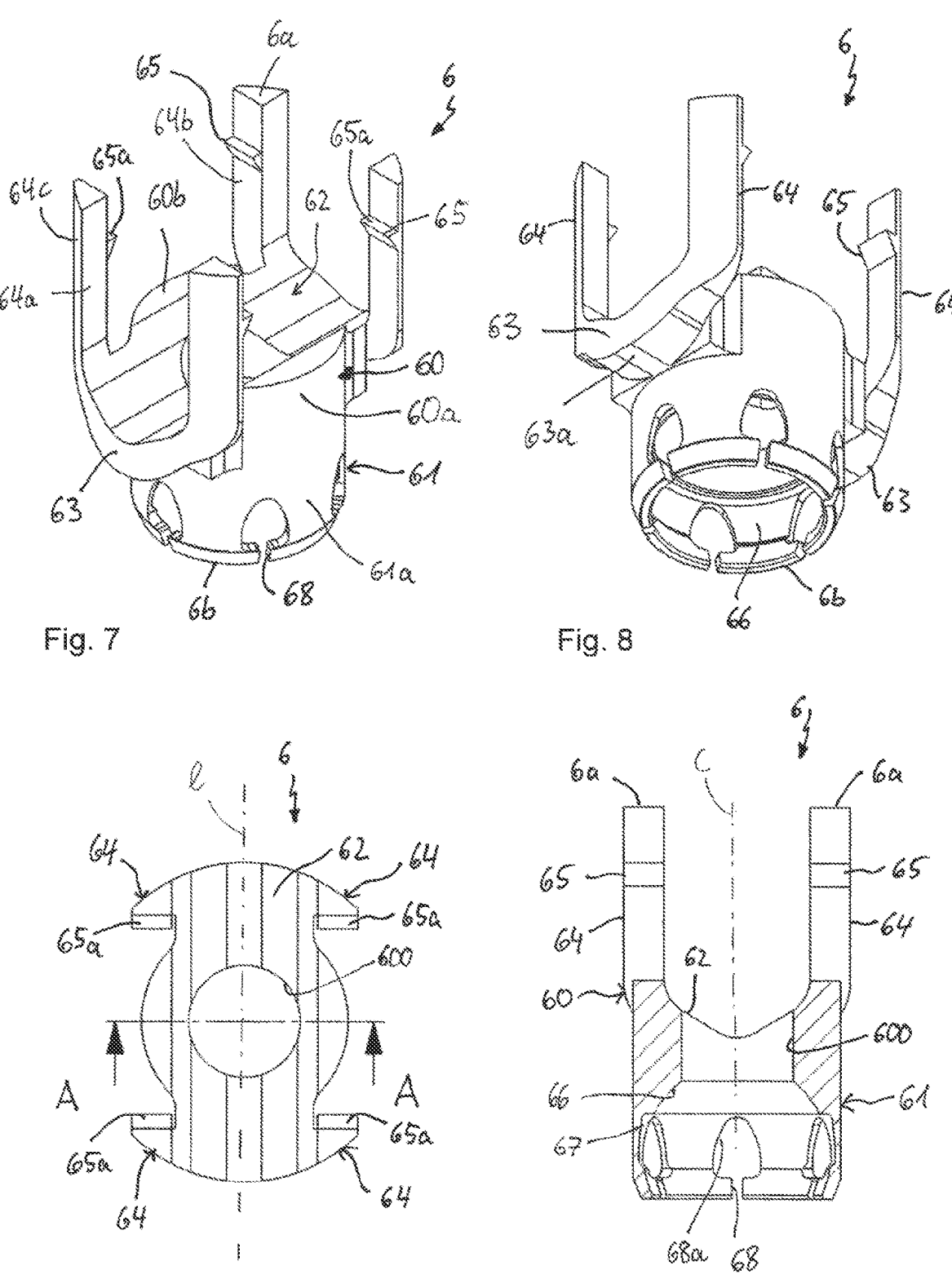
FIG. 7 shows a perspective view from a top of a pressure member of the polyaxial bone anchoring device of FIGS. 1 and 2.
FIG. 8 shows a perspective view from a bottom of the pressure member of FIG. 7.
FIG. 9 shows a top view of the pressure member of FIGS. 7 and 8.
FIG. 10 shows a cross-sectional view of the pressure member of FIGS. 7 to 9, the cross-section taken along line A-A in FIG. 9.

In a region adjacent to the first end 5a of the receiving part 5, a substantially U-shaped recess 53 extends from the first end 5a in the direction of the second end 5b. The width of the recess 53 may be slightly greater than a diameter of the rod 200 to be inserted, such that the rod 200 can be placed in the recess 53 and can be guided therein. By means of this, the recess 53 forms a rod receiving recess or a channel for the rod, wherein the sidewalls of the channel form two free legs 54. The longitudinal axis L of the channel extends substantially perpendicular to the central axis C. As best seen in FIGS. 3 and 5, on each side of the legs 54 in the longitudinal direction, a recess 55 is formed. The recess 55 decreases the width of the legs 54 in the longitudinal direction L of the channel, or in other words, in the circumferential direction of the receiving part 5. The recess 55 starts at the first end 5a and extends in the axial direction, e.g., parallel to the central axis C up to a position between a bottom 53a of the recess 53 and the second end 5b. A depth of the recesses 55 in the longitudinal direction L of the channel is such that a portion of the pressure member 6 can be placed in the recess, preferably such that the portion does not extend beyond an outer cylindrical envelope of the receiving part 5.

At the free edges 54a of each of the legs 54, recesses 56 are formed, respectively, that serve for engagement with a portion of the pressure member 6 to form an abutment for limiting movement of the pressure member 6 towards the first end 5a. The recesses 56 may be provided in an upper region of the free edges 54a of the legs 54, preferably at a small distance from the first end 5a. The shape of the recesses 56 may be substantially rectangular. Preferably an upper or higher downwardly facing boundary wall 56a of the recesses 56 is substantially flat and extends substantially perpendicular to the central axis C. Within the recesses, a lip 56b may be provided that divides the recesses 56 into an upper and lower compartment. A lower wall 56c of the lip 56b forms an abutment for a portion of the pressure member 6. The lip 56b may have an outer contour that does not protrude out of the recess 56. As can be seen in particular in FIGS. 3 and 5, each leg 54 has one recess 56 at each of its free edges 54a, so that the recesses 56 of one leg 54 are open to opposite sides of the leg.

On the outer surface of each leg 54, at a height that is above the bottom 53a of the substantially U-shaped recess 53, a protrusion 57 is formed on the outer wall that serves as an engagement portion for engaging the receiving part 5 with an instrument. The protrusion 57 is arranged at a center of the leg in a circumferential direction, and has a substantially trapezoidal shape in a side view as depicted in FIG. 5, with the smaller tip portion pointing towards the first end 5a. By means of such a shape, engagement with an instrument may be facilitated. The protrusion 57 is surrounded by an axial recess 58, the circumferential width of which corresponds to the circumferential width of the base of the protrusion 57. The recess 58 is open towards the first end 5a to allow the instrument to be slid onto the receiving part.

Referring additionally to FIGS. 7 to 10, the pressure member 6 will be described in greater detail. The pressure member 6 includes a first end 6a that forms an upper end and a second end 6b that forms a lower end. An upper portion 60 of the pressure member forms a rod receiving portion, and lower portion 61 of the pressure member forms a head receiving portion. An outer surface 61a of the head receiving portion 61 is substantially cylindrical, with a diameter such that the pressure member 6 can be placed into the passage 50 and can move in the coaxial bore 50a of the receiving part. When the pressure member 6 is mounted to the receiving part 5, a central axis of the pressure member coincides with the central axis C of the receiving part. In the rod receiving portion 60 a rod support surface 62 is formed that extends concavely in the axial direction of the central axis C from an upper end 60b of the cylindrical portion 60a to a distance therefrom in the direction of the second end 6b. In the direction transverse, more specifically perpendicular to the central axis C, the rod support surface has a longitudinal axis I. The rod support surface 62 is extended with extensions 63 in the direction of the longitudinal axis I beyond the cylindrical portion 60a of the pressure member 6. A length of the extensions 63 in the direction of the longitudinal axis I is such that when the pressure member 6 is placed in the receiving part, the extensions 63 extend out of the space confined by the legs 54 of the receiving part into the U-shaped recess 53. In greater detail, the extensions 63 are configured to be received in the recesses 55 at both sides of the legs 54. A lower side 63a of each of the extensions faces towards the second end 5b of the receiving part. The rod support surface 62 may have a V-shaped cross-section in a direction transverse to the longitudinal axis I to permit support of rods of different diameters. However, the rod support surface can also be flat or cylindrical, or can have any other shape.

At the outermost end of each of the extensions 63 when viewed in the direction of the longitudinal axis I of the rod support surface 62, a pair of columns 64 or arms is formed that constitute an engagement portion configured to cause the pressure member to exert pressure on the head when engaged. Hence, the pressure member 6 in total has four upstanding columns 64. Each pair of columns 64 sandwiches the end of the rod support surface 62 therebetween. The upper end surface of the upstanding columns 64 forms the first end 6a of the pressure member 6. This upper end surface 6a constitutes an engagement surface for an instrument. A distance between two columns 64 of one pair of columns in a direction perpendicular to the longitudinal axis corresponds to a maximum diameter of a rod that can be inserted and supported on the rod support surface 62. The cross-section of the columns when viewed in the axial direction of the central axis C may be substantially triangular. More specifically, sidewalls 64a of the columns 64 that are facing towards each other and that extend in a direction substantially parallel to the longitudinal axis I may be substantially flat. Similarly, sidewalls 64b of the columns 64 that are facing towards each other in the longitudinal direction and that extend substantially perpendicular to the longitudinal axis I may also be substantially flat. The outer surface 64c of each of the columns 64 is substantially cylinder segment-shaped and may be flush with an outer cylindrical surface of the receiving part 5 when the pressure member 6 is arranged in the receiving part. At each of the sidewalls 64b that extend substantially perpendicular to the longitudinal axis I, a protrusion 65 is formed that is configured to engage the recess 56 provided at the legs 54 of the receiving part, respectively. The protrusion 65 may be a rib that extends substantially transverse to the longitudinal axis I and that may have a substantially triangular cross-section with an upper face 65a that extends substantially perpendicular to the central axis C. The height of the columns 64 may preferably be such that the upper end 6a is at the same height or protrudes above a rod 200 with a greatest possible diameter that is configured to be placed on the rod support surface 62. More preferably, the upper end 6a of the columns 64, when the pressure member 6 is inserted into the receiving part and is in a pre-locking position as explained below, extends up to the upper end 5a of the receiving part or protrudes slightly above the upper end 5a. The ribs 65 are at an axial position that permits them to enter the upper and lower compartment of the recess 56 at the legs 54 of the receiving part 5.

In the lower portion 61 of the pressure member 6, a head receiving recess 66 is provided for the head 3 of the bone anchor 1. The head receiving recess 66 may be substantially spherically-shaped with a radius corresponding to that of the head 3, and is configured to extend over the region of the head 3 with the greatest outer diameter E. At a distance from the second end 6b, the head receiving recess 66 may have an additional slightly conically-shaped recess 67 that widens towards the second end 6b and that is sandwiched in the axial direction between the spherical portions of the head receiving recess 66. The conical recess 67 may render the head receiving portion 61 more flexible. The lower portion of the head receiving portion 61 also has a plurality of slits 68 that are open to the second end 6b. The number and dimensions of the slits 68 are such that the wall confining the head receiving recess 66 can expand to snap onto the head 3 when the head 3 is inserted. To increase flexibility, the closed end portions 68a of the slits 68 may be widened. An outer surface portion 69 adjacent to the second end 6b of the pressure member 6 may be tapered, for example, conically tapered. The outer surface portion 69 is configured to cooperate with the narrowing portion 50c of the passage of the receiving part 5. Lastly, a coaxial bore 600 in the pressure member 6 permits access to the head 3 with a drive tool.

The pressure member 6 may be preassembled with the receiving part 5. For mounting, the pressure member 6 is inserted through the first end 5a into the passage 50 of the receiving part 5 until the head receiving recess 66 extends into the second coaxial bore 50b. Since the rod support surface 62 is aligned with the substantially U-shaped recess 53, the extensions 63 with the columns 64 automatically enter the recesses 55 of the receiving part 5.

The coupling device preassembled in this way can be mounted to the bone anchor 1 either outside a patient's body or in-situ after the bone anchor 1 has been inserted into bone or a vertebra.

Figures 12A, 12B, 12C, 12D:
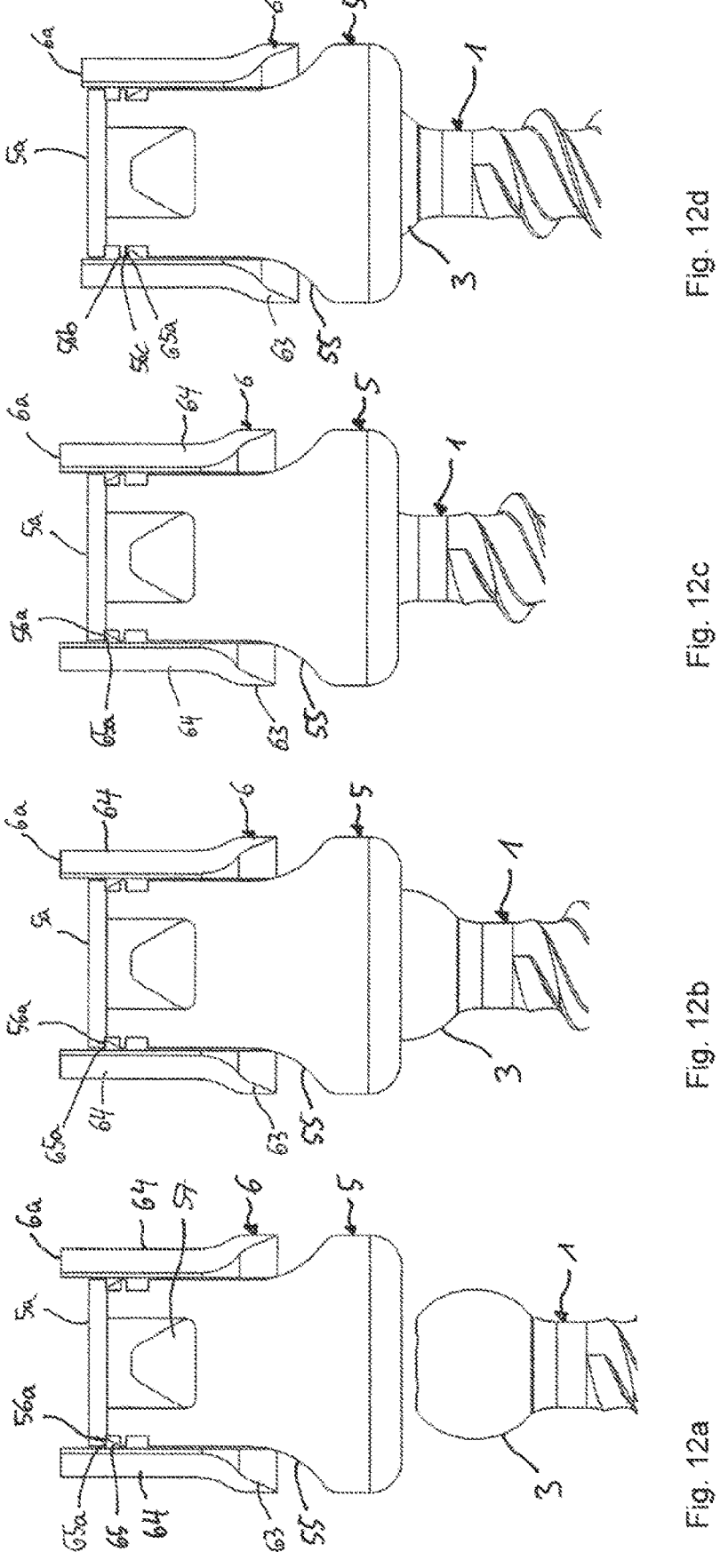
FIGS. 12*a* to 12*d* show side views of steps of mounting the coupling device of FIGS. 1 and 2 to a bone anchor of FIGS. 1 and 2 and of pre-locking a head of the bone anchor in the coupling device.
Figures 13A, 13B, 13C, 13D:
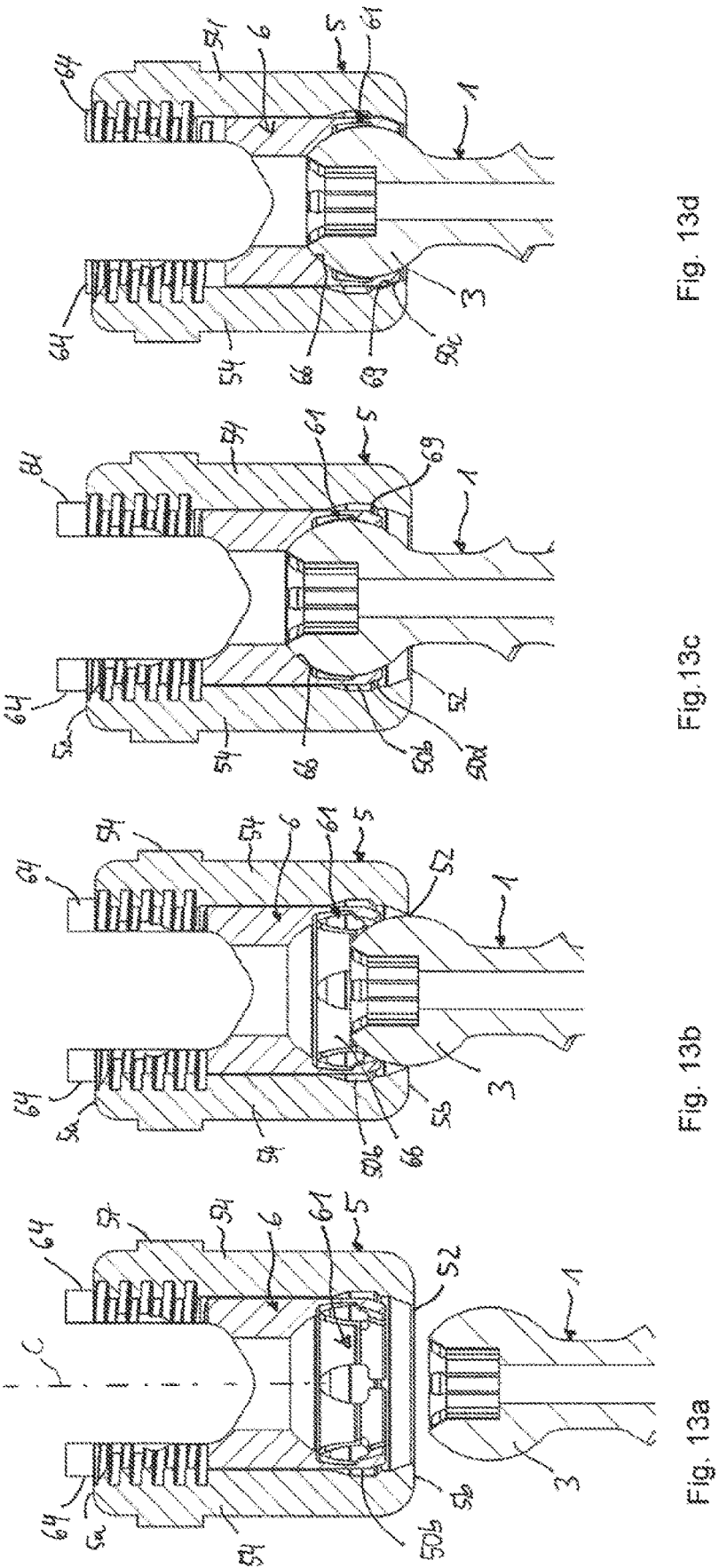
FIGS. 13*a* to 13*d* show cross-sectional views of the steps of mounting the coupling device to the bone anchor corresponding to FIGS. 12*a* to 12*d*, the cross-sections taken in a plane including the central axis of the receiving part and extending through centers of opposite legs of the receiving part.

Assembly of the coupling device and the bone anchor will be described, referring to FIGS. 12a to 12d and the corresponding cross-sectional illustrations FIGS. 13a to 13d. First, as shown in FIGS. 12a and 13a, the pressure member is in an insertion position where the head receiving recess 66 is at least partially within the widened portion or second coaxial bore 50b of the passage 50. The upper surfaces 65a of the protrusions 65 are in the upper compartment of the recess 56 on the legs 54, respectively. The coupling device is oriented with the second end 5b of the receiving part 5 towards the head 3 of the bone anchor.

Next, as shown in FIGS. 12b and 13b, the head 3 is inserted through the opening 52 at the second end 5b into the receiving part 5, and more particularly into the head receiving recess 66 of the pressure member 6. While the head 3 enters the head receiving recess, the pressure member 6 assumes an insertion position in which the upper surfaces 65a of the protrusions 65 abut against the lower wall 56a of the recess 56 in the receiving part. Thus, the lower wall 56a acts as a stop and prevents further upward movement of the pressure member 6, so that the pressure member 6 cannot be pushed out through the first end 5a of the receiving part. The upper end 6a of the pressure member projects above the first end 5a of the receiving part 5.

Then, as shown in FIGS. 12c and 13c, the head 3 has fully entered the head receiving recess 66 of the pressure member. Due to the flexibility of the pressure member 6 in the region of the head receiving recess 66, the pressure member 6 can snap on the head 3. The widened portion 50b of the passage 50 in the receiving part provides space for expansion of the pressure member 6 therein when the head 3 is inserted. Depending on the size of the head receiving recess 66 relative to the head 3, the head 3 may be held by friction in the head receiving recess 66.

Finally, as shown in FIGS. 12d and 13d, the pressure member 6 is moved downward towards the second end 5b of the receiving part 5. Alternatively, when the bone anchor 1 has already been inserted into bone, the receiving part 5 can be pulled upwards relative to the bone anchor 1. By means of this, the outer surface portion 69 of the pressure member 6 enters the narrowing portion 50c of the passage 50, whereby the head 3 is prevented from being removed through the opening 52. This constitutes a pre-locking position of the pressure member. Due to the inclined lower wall of the protrusions 65, the protrusions 65 can move out of the upper compartment of the recess 56 and slide over the lip 56b into the lower compartment of the recess 56 where the upper surface 65a of the protrusion 65 abuts against the lower wall 56c of the lip 56b. Thus, the lip 56b provides a stop against upward movement of the pressure member 6 out of the pre-locking position. When the pressure member is pushed into the narrowing portion 50c, the conical outer surface portion 69 of the pressure member may pass the edge 50d, which additionally contributes to compressing the head receiving portion 61 around the head 3. Preferably, in the pre-locking position, the head 3 may additionally be clamped by friction and temporarily held at an angular position, while still being pivotable prior to final locking.

Referring to FIGS. 14 to 20, an instrument which is suitable for use with the bone anchoring device described above will be explained. The instrument 100 includes an outer member 110 and an inner member 120 movable, more specifically displaceable, relative to the outer member 110.

A handle and/or actuating device including, for example, a rotating knob 130 may be provided for displacing the inner member relative to the outer member. Various other mechanisms may be implemented to displace the inner member 120 relative to the outer member 110 in other embodiments. An overall shape of the inner and outer members is tubular, although the tubes may have slits so that they are not completely closed, and in addition, the tubes may have protrusions and/or recesses. The central longitudinal axes of the tubes coincide with the central axis C of the receiving part when the instrument 100 is attached to the receiving part 5.

Referring in greater detail to FIGS. 15 to 17, a front portion of the outer member 110 having an outermost front end 110a is shown in an enlarged view. The outer member 110 has the front end 110a, that in use faces towards the bone anchoring device 1. Two opposite slits 111 that are open at the front end 110a extend over a portion of the outer member 110, so that two arms 112 are formed that are flexible at least so that they can spread apart to engage the protrusions 57 at the receiving part 5. The width of the longitudinal slits 111 may be at least as large as the greatest diameter of a rod to be inserted into the receiving part. This permits use of the instrument when a rod is already inserted or when the rod has to be inserted while the instrument is already attached. An inner diameter of the front portion between the arms is such that the front portion can be placed over the receiving part 5 so that the front portion encircles an upper portion of the receiving part including the columns 64 of the pressure member. At a distance from the front end 110a, recesses 113 are formed in a circumferential direction on both sides of each arm. The recesses 113 are open towards the slits 111 and are arranged in a manner such that two recesses 113 on opposite arms 112 are facing each other, respectively. When the outer member 110 is placed on the receiving part such that the slits 111 are aligned with the U-shaped recess 53, the recesses 113 are at positions corresponding to the free edges 54a of the legs 54 of the receiving part, and extend with their upper end above the first end 5a of the receiving part and with their lower end preferably to some extent below the first end 5a of the receiving part. A contour of the recesses is adapted to receive a portion of the inner member 120, so that the portion of the inner member can move therein up and down when the inner member is displaced relative to the outer member. In the embodiment, the contour is substantially rectangular.

Furthermore, at a distance from the front end 110a, an engagement recess 114 is provided on each arm 112. The engagement recess 114 is located on each arm 112 at a position for engaging the protrusion 57 on the receiving part 5 when the outer member 110 is placed onto the receiving part 5. Moreover, the contour of the engagement recesses 114 substantially matches the contour of the engagement protrusions 57, so that a form-fit engagement can be achieved.

Figures 21A, 21B, 21C, 21D:
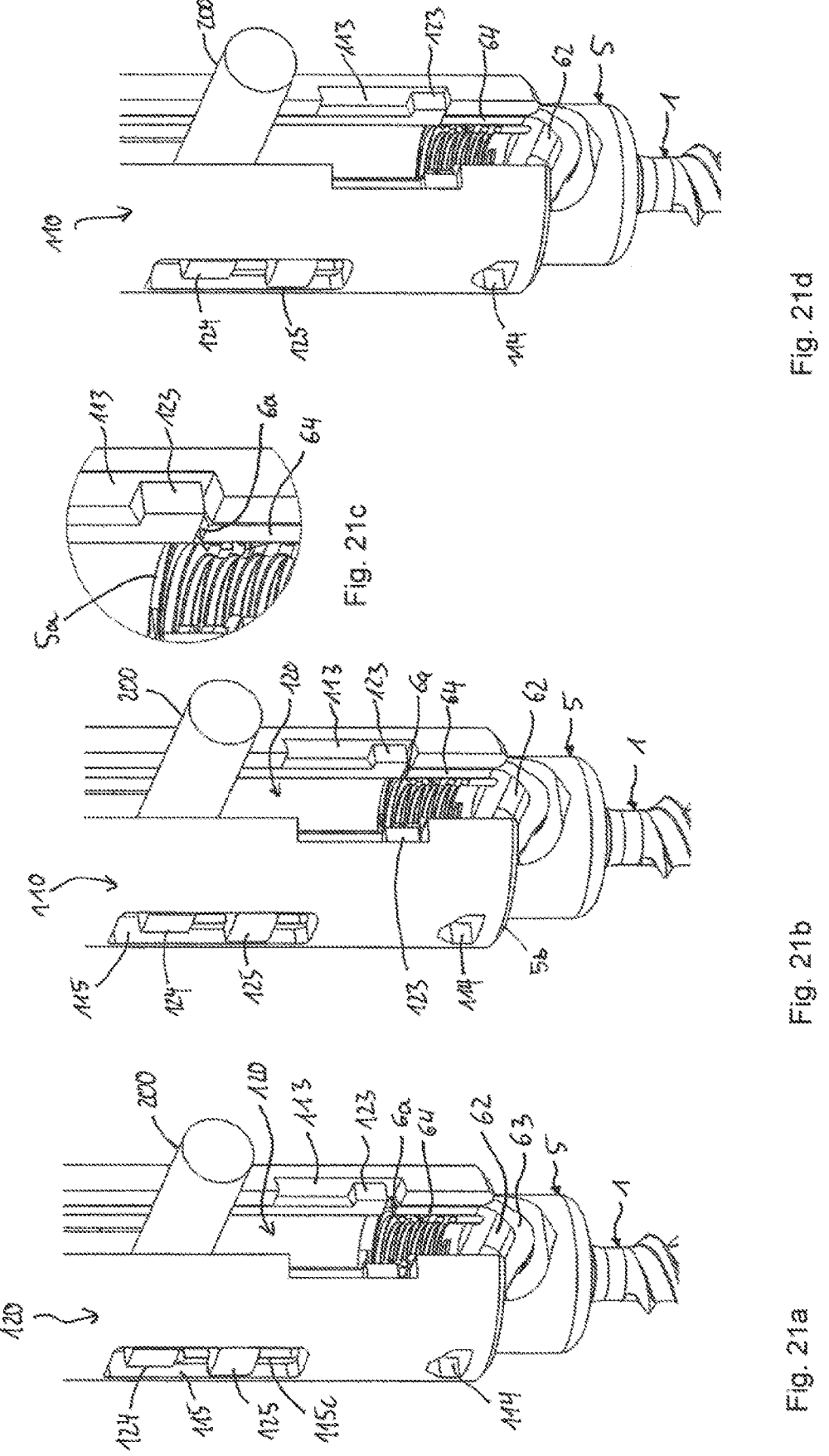

At substantially a center of each of the arms 112 in the circumferential direction, an axially elongate guiding recess 115 is formed that is sized and shaped to provide guidance for a protrusion of the inner member 120. In greater detail, each recess 115 has an upper region 115a and a lower region 115b that is narrower with respect to the upper region 115a. This is achieved by two wings 115c that extend from the longitudinal sides of the recess 115 towards the middle in the circumferential direction. The wings 115c have a distance from the outer surface of the front portion such that, as depicted in FIG. 21a, for example, a portion of the inner member 120 that extends between the wings 115c is still located within the recess 115, or in other words, does not protrude substantially to the outside.

Figure 18:
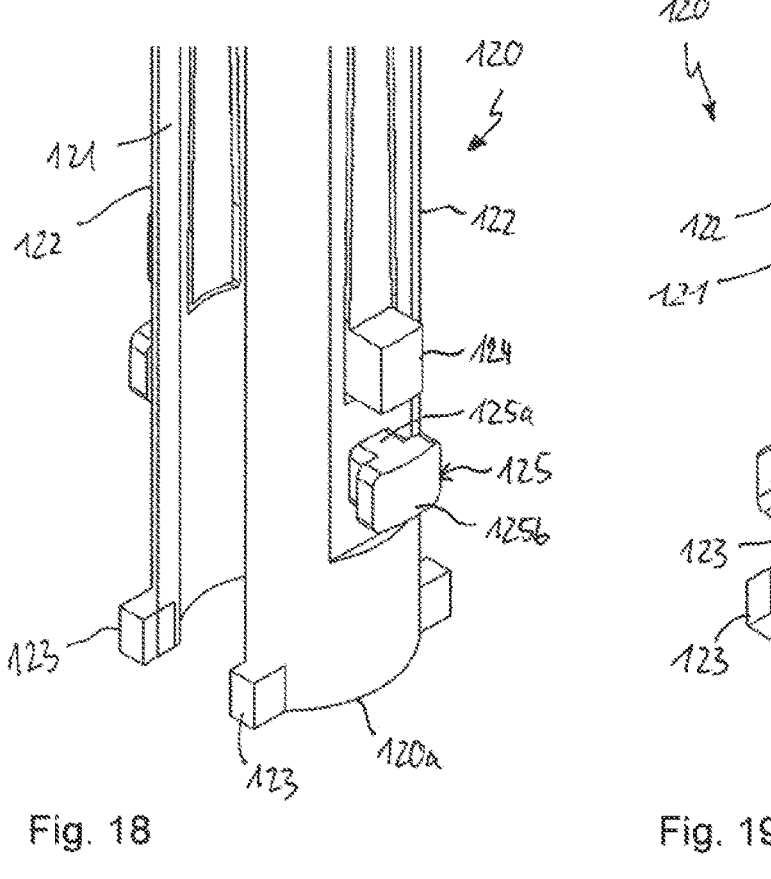
FIG. 18 shows a perspective view from a top of a front portion of an inner member of the instrument of FIG. 14.
Figure 19:
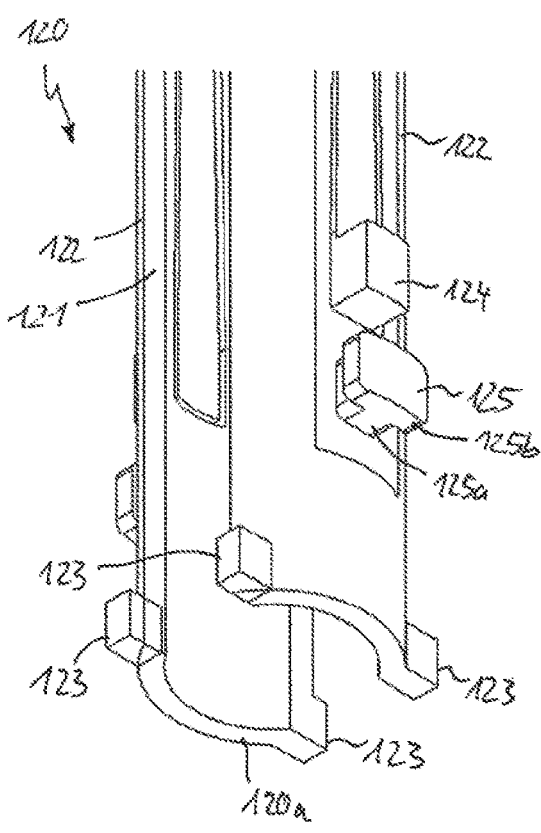
FIG. 19 shows a perspective view from a bottom of the front portion of FIG. 18.
Figure 20:
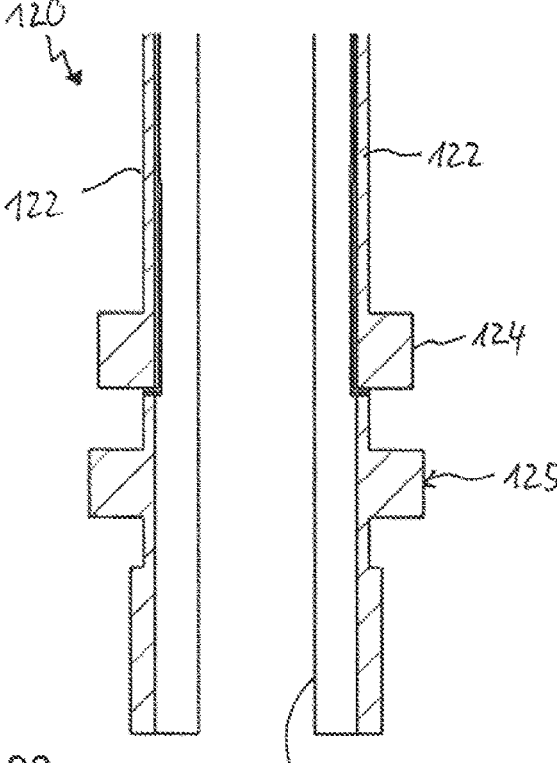
FIG. 20 shows a cross-sectional view of the front portion of the inner member of FIGS. 18 and 19, the cross-section taken in a plane including the central longitudinal axis of the instrument and extending through centers of two arms of the front portion.

A front portion of the inner member 120 is illustrated in greater detail in FIGS. 18 to 20. The inner member 120 has an outer diameter that permits the inner member to extend through the outer member 110. Opposite elongate slits 121 extend from the front end 120a of the inner member over a length so that two arms 122 are formed. The width of the slits 121 is at least as large as the greatest diameter of a rod to be inserted into the receiving part. Each of the arms 122 includes, at the front end adjacent to the slit, an extension 123 that protrudes outwardly and away from the arm in a direction substantially parallel to a plane that includes the central axis C and extends through centers of the opposite slits 121. When the inner member 120 is in the outer member 110 and the outer member is placed on the receiving part and engages the protrusions 57 with the recesses 114, the extensions 123 are located outside the legs 54 of the receiving part in a circumferential direction, such that the extensions are configured to press onto the upper end 6a of the columns 64 of the pressure member 6. The extensions 123 have a shape such that the extensions can be received in the recesses 113 of the outer member 110. In the embodiment, the extensions 123 are substantially cuboid.

Figure 14:
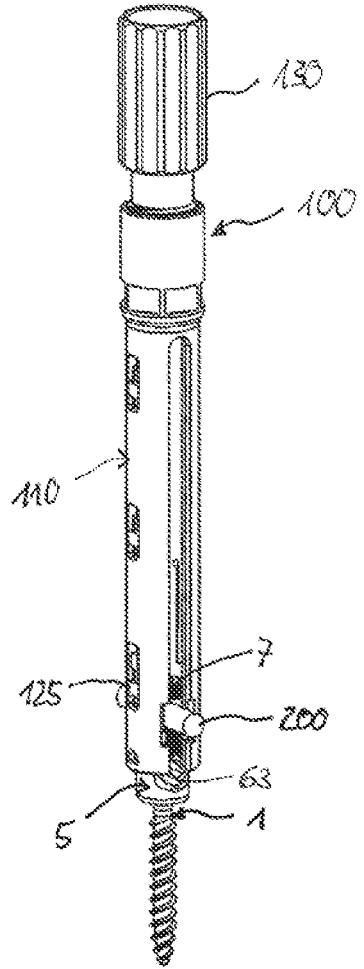
FIG. 14 shows a perspective view of a system including the polyaxial bone anchoring device of FIGS. 1 to 13*d*, and an instrument attached thereto, and with an inserted rod.

At the center of each of the arms 122 in the circumferential direction, two axially spaced apart protrusions 124, 125 are formed that are configured to engage the elongate recesses 115 on the arms 112 of the outer member 110. The first protrusions 124 may be substantially cuboid-shaped and are configured to be received in the upper portion 115a of the recess 115 of the outer member 110. The second protrusion 125 is spaced apart from the first protrusion 124 towards the front end 120a and includes a narrower neck portion 125a and a substantially plate-shaped head 125b. The neck portion 125a is configured to be guided between the wings 115c, and the head portion 125b is configured to extend over the wings 115c. When the inner member 120 is in the outer member and the extensions 123 extend into the recesses 113, an axial movement of the inner member relative to the outer member 110 is limited by the axial movement of the first protrusion 124 in the upper region 115a of the elongate recess 115. The extensions 123 can be moved toward the front end 110a of the outer member 110 until the first protrusion 124 abuts against the wings 115c. It shall be noted that, along the arms of the inner member and the outer member, further protrusions and recesses may be formed as shown in FIG. 14. The displacement of the inner member relative to the outer member can be effected using the rotating knob or handle 130.

The parts and portions of the bone anchoring device and the instrument may be made of any material, preferably however, of titanium or stainless steel, or of any bio-compatible metal or metal alloy or plastic material. For bio-compatible alloys, a NiTi alloy, for example Nitinol, may be used. Other materials that can be used are magnesium or magnesium alloys. Bio-compatible plastic materials that can be used may be, for example, polyether ether ketone (PEEK) or poly-L-lactide acid (PLLA). The parts can be made of the same or of different materials from another.

Use of the instrument together with the bone anchoring device will be described, referring to FIGS. 21a to 22c. In clinical use, usually two or more bone anchoring devices that are to be connected through the rod 200 are anchored in bone or in vertebrae. The pressure member may be in the pre-locking position as shown in FIGS. 12d and 13d. In a first step, shown in FIG. 22a, the instrument is oriented such that the slits 111, 121 are aligned with the U-shaped recess 53 of the receiving part. Next, as shown in FIG. 21a, the engagement recesses 114 engage the protrusions 57 of the receiving part. The groove 58 facilitates the sliding down of the outer member until the recess 114 snaps over the protrusion 57. The inner member 120 is in a retracted position, which means that the extensions 123 are located at a distance from the upper end 6a of the columns 64 of the pressure member 6. The outer member 120 tightly fits around the receiving part.

Figure 22C:
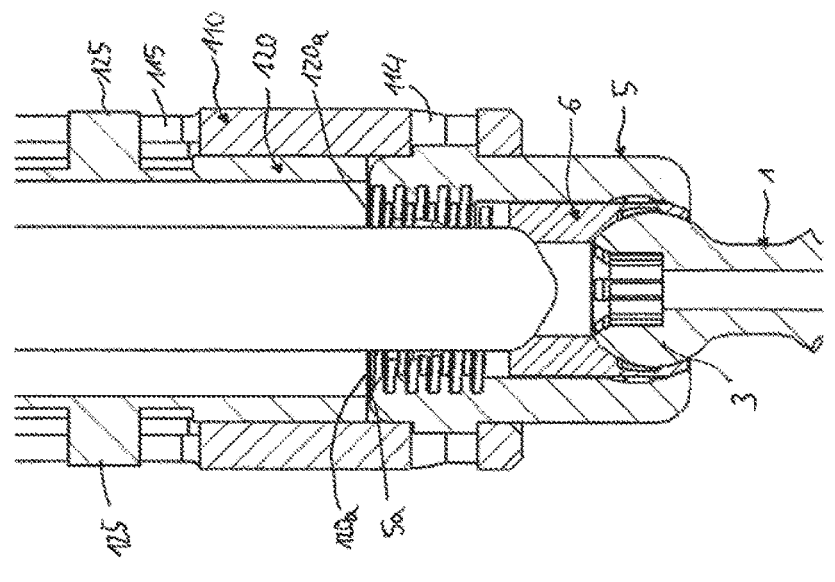
FIGS. 22*a* to 22*c* show cross-sectional views of attaching the instrument of FIGS. 14 to 20 to the polyaxial bone anchoring device of FIGS. 1 and 2.
Figure 22B:
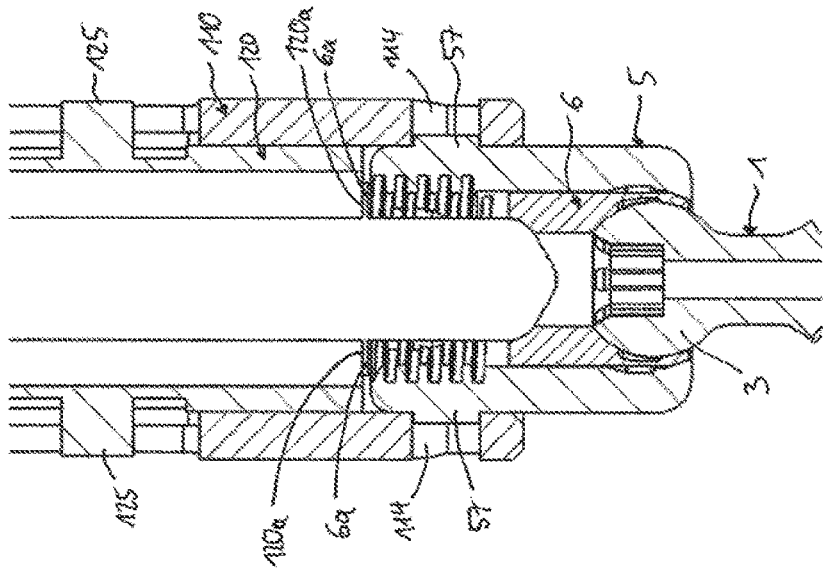
Figure 22A:
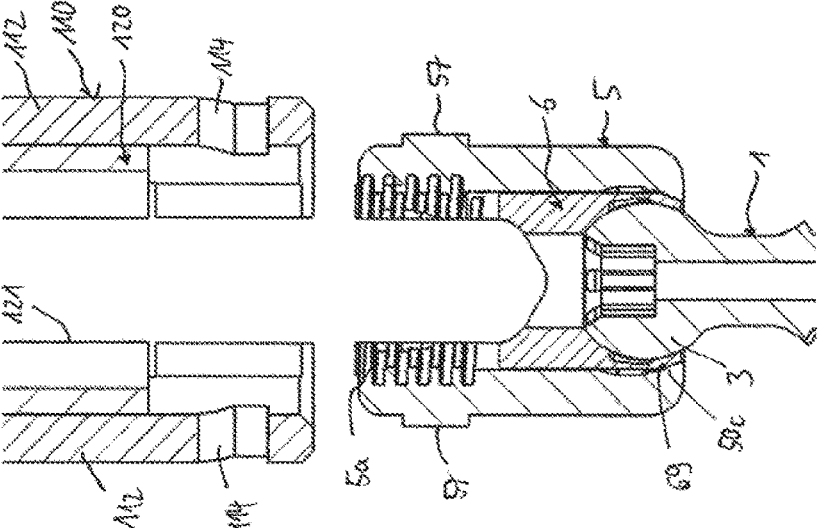
Figure 23:
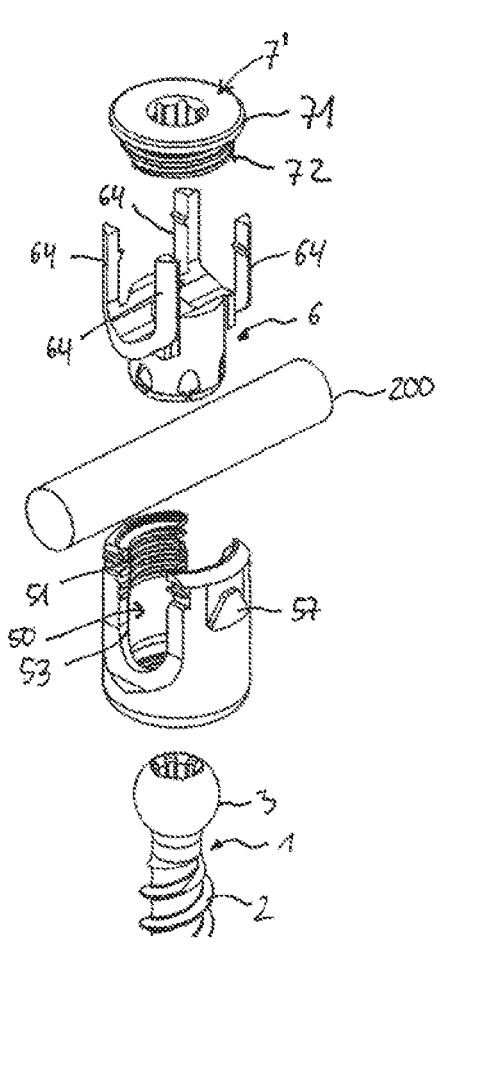
FIG. 23 shows a perspective exploded view of a polyaxial bone anchoring device according to a second embodiment.
Figure 24:
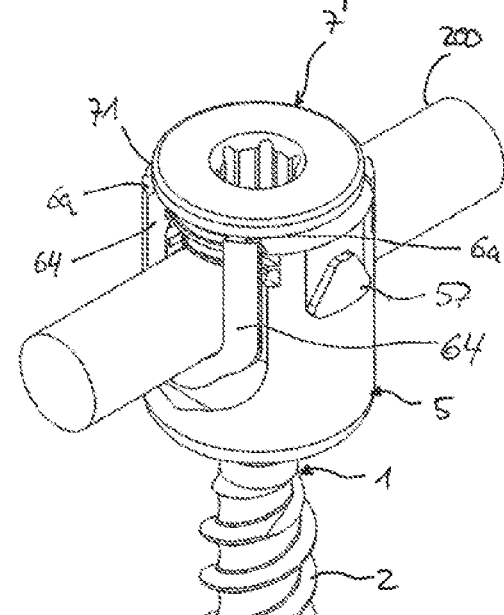
FIG. 24 shows a perspective view of the polyaxial bone anchoring device of FIG. 23 in an assembled state.
Figure 25:
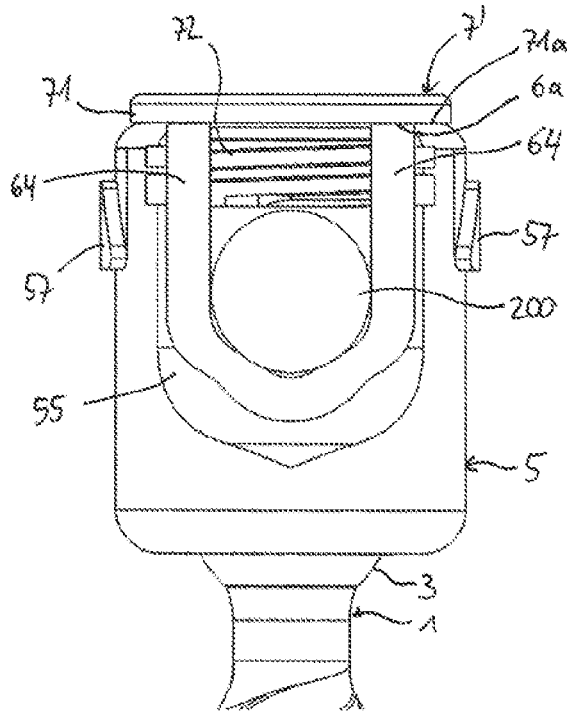
FIG. 25 shows a side view of the polyaxial bone anchoring device of FIGS. 23 and 24 in the assembled state.
Figure 26:
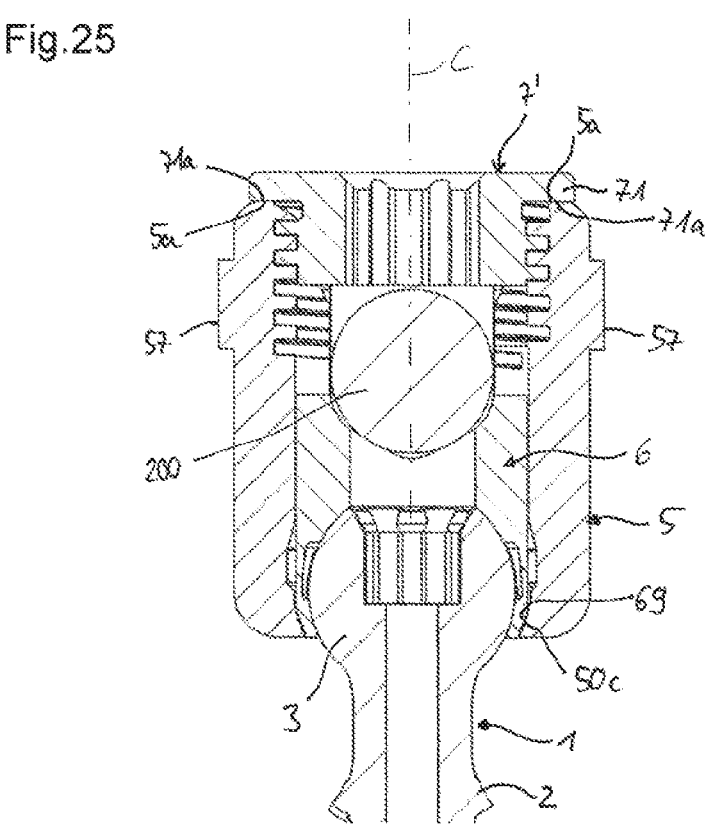
FIG. 26 shows a cross-sectional view of the polyaxial bone anchoring device of FIGS. 23 to 25, the cross-section taken in a plane including a central axis of a receiving part of the polyaxial bone anchoring device and extending through centers of the legs of the receiving part.

Thereafter, as shown in FIGS. 21b, 21c and 22b, the inner member 120 is moved downward until the extensions 123 press onto the upper surface 6a of the columns 64. As a result, the pressure member 6 is pressed deeper into the narrowing portion 50c until the head 3 of the bone anchor is clamped or even locked, as shown in FIGS. 21d and 22c.

The locking of the head can also be released, for example, when the inner member is moved back to the retracted position and the pressure member moves upwards again. In other words, the pressure of the pressure member onto the head decreases to render the head pivotable. Since the extensions 63 are at the outside of the legs 54, the extensions can also be easily gripped with an additional instrument or by hand to push the pressure member back to the pre-locking position.

The rod and a fixation member may be inserted between the legs 54. For finding a suitable angular relationship between the bone anchor and the receiving part, the rod 200 does not need to be in the rod channel, nor is a fixation element necessary at this stage. However, since the instrument engages the pressure member outside the rod channel, the adjustment of the polyaxial angle can also be made with the rod inserted into the channel, either at the bottom thereof or at a higher position. Also the fixation member 7 may already be present during adjusting of the angular position or can be introduced through the inner member 120 of the instrument into the receiving part later. Hence, the rod or the fixation member can be inserted before or after correction steps or the locking of the polyaxial angle.

A second embodiment of the polyaxial bone anchoring device will be described, referring to FIGS. 23 to 26. In the second embodiment, the bone anchor, the receiving part and the pressure member are identical to that of the first embodiment. Instead of the fixation member 7, a closure member 7' is used for locking the head 3. The closure member 7' has an annular rim 71 adjacent a threaded portion 72 that cooperates with the inner thread 51 of the receiving part 5. The annular rim 71 has a lower side 71a with an outer diameter that is greater than an inner diameter of the first coaxial bore 50a of the receiving part. By means of this, the annular rim 71 can be screwed in only until the lower side 71a presses on the upper end 5a of the receiving part 5. The axial length of the threaded portion 72 of the closure member 7' is such that, when the closure member 7' presses onto the upper end 5a of the receiving part, a lower surface 72a of the threaded portion 72 can be located at a distance from the uppermost portion of an inserted rod 200 that rests on the rod support surface 62 of the pressure member 6.

In use, when the closure member 7' is inserted and screwed between the legs 54, the lower surface 71a of the annular rim 71 contacts the upper surface 6a of the columns 64. Tightening the closure member 7' moves the pressure member 6 downward until the head 3 is locked. At the same time, the lower side 71a of the annular rim 71 abuts against the upper end 5a of the receiving part 5. As a result, the rod is still movable in the rod channel. Hence, the closure member 7' can be used for locking the head 3 while keeping the rod movable. This may be suitable, for example, for growing rod applications.

In a further modification, a two-part closure member (not shown) may be provided which is similar to the closure member 7', but which includes an additional inner set screw in the closure member which can be independently tightened so that it contacts the rod and fixes the rod.

Other modifications of the embodiments described are also possible. The features of one embodiment can also be combined with those of another embodiment to produce a variety of still further embodiments. The parts are not limited to their detailed shape as depicted in the embodiments.

For example, the bone anchoring device is shown to be a bottom-loading bone anchoring device, where the head 3 is inserted from the second or lower end into the receiving part. The bone anchoring device in other embodiments may, however, be a top-loading bone anchoring device, where the bone anchor is inserted from the first end or top end into the receiving part. In such a case, the pressure member may have a slightly different design that covers the upper portion of the head and presses the head against a seat provided in the receiving part. For the bone anchor, all kinds of bone anchors such as screws, nails, hooks, etc., cannulated or not cannulated, may be used.

The pressure member may also have a different design, for example, only one or less than four of the columns may be necessary to achieve the described effects. The shape of the columns may also be different.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A coupling device for coupling a rod to a bone anchor, the coupling device comprising:
   a receiving part configured to receive a head of the bone anchor, the receiving part having a first end and a second end, a central axis that extends between the first end and the second end, and two legs at the first end that define a recess for receiving the rod, wherein the recess extends in a longitudinal direction transverse to the central axis; and
   a monolithic pressure member positionable at least partially in the receiving part to exert pressure on an inserted head, the pressure member comprising a body that defines a rod support surface for supporting the rod and four arms, wherein each of the four arms is flexible and extends circumferentially around the central axis from a first end that is connected axially to another portion of the pressure member to a free second end that is configured to be positioned laterally outwardly from the body and at a different axial position than the entire rod support surface.

2. The coupling device of claim 1, wherein the four arms are engageable for adjusting the pressure member to exert pressure on the head.

3. The coupling device of claim 2, wherein the four arms are configured to engage another part of the coupling device.

4. The coupling device of claim 2, wherein the four arms are configured to engage an outside instrument.

5. The coupling device of claim 1, wherein when the pressure member is assembled with the receiving part, at least part of each of the four arms is positioned outside the legs of the receiving part in the longitudinal direction.

6. The coupling device of claim 1, further comprising a compressible surface forming a seat for the head that is configured to exert upward pressure on the head to lock the head in the receiving part.

7. The coupling device of claim 6, wherein the compressible surface is formed as part of the pressure member and defines a head receiving recess for receiving the head of the bone anchor.

8. The coupling device of claim 1, wherein when the pressure member is assembled with the receiving part, the free second end of each of the four arms is located farther away from the second end of the receiving part than the first end of each of the four arms is from the second end of the receiving part.

9. The coupling device of claim 1, wherein the body comprises a substantially cylindrical outer surface, and wherein at least part of each of the four arms is positioned laterally outwardly from the substantially cylindrical outer surface.

10. The coupling device of claim 1, wherein the receiving part defines an opening at the second end sized to facilitate insertion of the head of the bone anchor from the second end into the receiving part.

11. The coupling device of claim 1, wherein when viewed in a cross-section perpendicular to the central axis, a radially outwardly facing surface of each of the four arms extends circumferentially around the central axis in a curved manner.

12. A bone anchoring device comprising:
a bone anchor comprising a head and a shank configured to be anchored in bone or in a vertebra; and
a coupling device for coupling a rod to the bone anchor, the coupling device comprising:
a receiving part configured to receive the head of the bone anchor, the receiving part having a first end and a second end, a central axis that extends between the first end and the second end, two legs at the first end that define a recess for receiving the rod, wherein the recess extends in a longitudinal direction transverse to the central axis, and an opening at the second end sized to facilitate insertion of the head from the second end into the receiving part; and
a monolithic pressure member positionable at least partially in the receiving part to exert pressure on the head, the pressure member comprising a body that defines a rod support surface for supporting the rod and four arms, wherein each of the four arms extends circumferentially around the central axis from a first end that is connected axially to another portion of the pressure member to a free second end that is positioned laterally away from the body;
wherein when the head and the pressure member are assembled with the receiving part, the pressure member is movable to a pre-locking position where the head is restricted from removal from the receiving part and each of the four arms is configured to engage a corresponding abutting surface portion on the bone anchoring device to hold the pressure member at the pre-locking position.

13. The bone anchoring device of claim 12, wherein the free second end of each of the four arms is configured to be positioned at a different axial position than the entire rod support surface.

14. The bone anchoring device of claim 12, wherein when the pressure member is at the pre-locking position, the head is held by friction in the receiving part to temporarily hold an angular position of the bone anchor relative to the receiving part.

15. The bone anchoring device of claim 12, wherein the abutting surface portions are formed on the receiving part, such that when the pressure member is at the pre-locking position, each of the four arms is configured to cooperate with the corresponding abutting surface portion on the receiving part to limit movement of the pressure member away from the second end of the receiving part.

16. The bone anchoring device of claim 12, wherein each of the four arms is flexible.

17. The bone anchoring device of claim 12, further comprising a compressible surface forming a seat for the head that is configured to exert upward pressure on the head to lock the head in the receiving part.

18. The bone anchoring device of claim 17, wherein the compressible surface is formed as part of the pressure member and defines a head receiving recess for receiving the head of the bone anchor.

19. The bone anchoring device of claim 12, wherein when viewed in a cross-section perpendicular to the central axis, a radially outwardly facing surface of each of the four arms extends circumferentially around the central axis in a curved manner.

20. A coupling device for coupling a rod to a bone anchor, the coupling device comprising:
a receiving part configured to receive a head of the bone anchor, the receiving part having a first end and a second end, a central axis that extends between the first end and the second end, and two legs at the first end that define a recess for receiving the rod, wherein the recess extends along a longitudinal axis that is transverse to the central axis, and wherein sides of the legs are recessed relative to an envelope defined by an outer surface of the receiving part such that the width of the legs is narrowed in a circumferential direction around the central axis; and
a monolithic pressure member positionable at least partially in the receiving part to exert pressure on an inserted head, the pressure member comprising a rod support surface for supporting the rod and an arm having a free end that is configured to be located at a different axial position than the entire rod support surface;
wherein when the pressure member is assembled with the receiving part, at least part of the arm of the pressure member is positioned outside a corresponding one of the legs of the receiving part and extends at least partially into the recessed region on the side of the corresponding one of the legs, while being aligned with the corresponding one of the legs in a direction parallel to the longitudinal axis and located substantially within the envelope defined by the outer surface of the receiving part.

* * * * *